United States Patent [19]

Fassihi

[11] Patent Number: 5,412,979
[45] Date of Patent: May 9, 1995

[54] METHOD AND APPARATUS FOR DISSOLUTION TESTING OF A DOSAGE FORM

[75] Inventor: Alireza D. Fassihi, Philadelphia, Pa.

[73] Assignee: Temple University - Of the Commonwealth System of Higher Education, Philadelphia, Pa.

[21] Appl. No.: 56,636

[22] Filed: May 3, 1993

[51] Int. Cl.$^6$ .............................................. B01D 11/02
[52] U.S. Cl. ..................... 73/53.01; 73/866; 73/64.55; 422/101; 424/449
[58] Field of Search ................. 73/866, 864.83, 863.23, 73/64.55, 53.01; 422/101, 102; 424/449

[56] References Cited

U.S. PATENT DOCUMENTS

| | | | |
|---|---|---|---|
| 3,791,221 | 2/1974 | Kirschner et al. | 73/432 |
| 3,791,222 | 2/1974 | Goodhart et al. | 73/432 |
| 3,802,272 | 4/1974 | Bischoff et al. | 74/432 |
| 4,681,858 | 7/1987 | Chaudhari et al. | 73/866 |

OTHER PUBLICATIONS

The United States Pharmacopeia XXII; The National Formulary XVII, The United States Pharmacopeial Convention, Inc., 1990, pp. xlii-xliv; 1577-1583.

*Primary Examiner*—Thomas P. Noland
*Assistant Examiner*—J. David Wiggins
*Attorney, Agent, or Firm*—Seidel Gonda Lavorgna & Monaco

[57] ABSTRACT

An apparatus and method determines the dissolution of a drug from a dosage form, most particularly a swellable dosage form. An inert, transparent cylindrical vessel having a hemispherical bottom contains a fluid medium. The dosage form is placed into the vessel. A disk carried in the vessel has a pair of annular rings for engaging the vessel walls spaced above the bottom of the vessel. The disk has a screen mesh circumferentially sandwiched by the rings for passage of the fluid medium through the disk. A dosage form retaining space defined between the disk and bottom of the vessel retains the dosage form. The disk restrains the dosage form from floating to the top of the fluid medium. A stirring mechanism having a vertical shaft and a blade at a lower end of the shaft is inserted into the vessel. The stirring mechanism rotates the fluid medium. The drug concentration in the fluid medium is sampled at selected time intervals.

13 Claims, 3 Drawing Sheets

METHOD AND APPARATUS FOR DISSOLUTION TESTING OF A DOSAGE FORM

FIELD OF THE INVENTION

This invention relates to a method and apparatus for testing the dissolution of a drug from a dosage form, such as a swellable gel-forming product, and more precisely to a method and apparatus for testing the dissolution of a dosage form which floats in a fluid medium.

BACKGROUND OF THE INVENTION

In the production of pharmaceutical dosage forms, the active ingredients are retained by inactive ingredients to facilitate the forming of a tablet or capsule that may be ingested and also to facilitate the metering of the dosage release. One aspect of dosage form development and quality control involves determining the release profile of the drug from the inactive carrier. The *United States Pharmacopeia* (*USP*) and the *National Formulary* have standards for testing the dissolution of the dosage form wherein the dosage form is placed in a fluid medium and the fluid is sampled at set intervals to determine the concentration of the active ingredient in the fluid.

Recently, modified release dosage forms based on gel formation have been developed. These dosage forms involve three dimensional swelling of the gel for subsequent drug release over periods of 1 to 24 hours. The gel-forming products acquire low density upon swelling and often float in the vessel when tested with standard dissolution test methods. To keep the object submerged, the *USP* recommends attaching a small loose piece of non-reactive material, such as a few turns of a wire helix. However, wire hinders the object's three-dimensional swelling in the fluid, thereby leading to release profiles with poor reproducibility. Moreover, some products contain three or more gel forming units enclosed within a capsule shell. Such products will not be retained with the wire helix once the gelatin shell is dissolved.

A dissolution testing method and apparatus is needed that does not add additional constraints to the dissolution of the dosage form.

SUMMARY OF THE INVENTION

This present invention provides an apparatus and method for testing dissolution of a drug from a dosage form, most particularly a swellable dosage form. An inert, transparent cylindrical vessel having a hemispherical bottom contains a fluid medium. The dosage form is placed into the vessel. A disk carried in the vessel has an annular ring assembly having an outwardly convex outer edge for contacting the vessel wall at a selected distance from the vessel bottom. The annular ring assembly has a pair of concentric mating annular rings. The disk has a screen mesh circumferentially sandwiched by the rings for passage of the fluid medium through the disk. A dosage form retaining spaced defined between the disk and bottom of the vessel retains the dosage form. The disk restrains the dosage form from floating to the top of the fluid medium. A stirring mechanism having a vertical shaft and a blade at a lower end of the shaft is inserted into the vessel. The stirring mechanism rotates the fluid medium. The drug concentration in the fluid medium is sampled at selected time intervals.

BRIEF DESCRIPTION OF THE DRAWINGS

For the purpose of illustrating the invention, there is shown in the drawings, a form which is presently preferred; it being understood, however, that this invention is not limited to the precise arrangement and instrumentality shown.

DESCRIPTION OF THE PREFERRED EMBODIMENT

Figure 1:
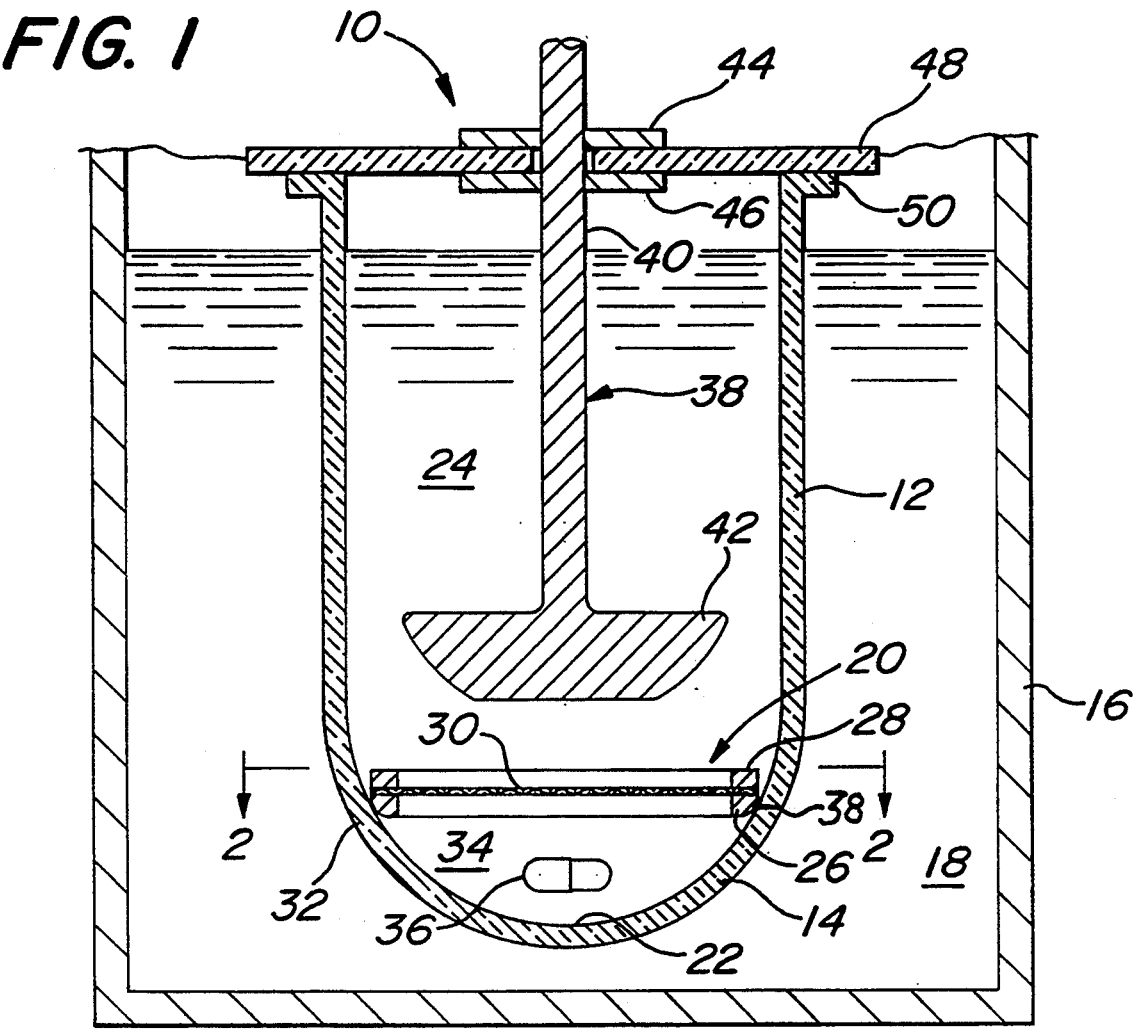
FIG. 1 is a side-sectional view of the testing apparatus.

Referring to FIG. 1, the test apparatus 10 has a cylindrical vessel 12 with a hemispherical bottom 14. The cylindrical vessel 12 is preferably made of glass or other inert, transparent material. The preferred dimensions are 160 mm to 175 mm high with an inside diameter of between 98 mm to 106 mm and nominal capacity of 1000 mL. The cylindrical vessel 12 is located in and spaced from a larger vessel 16 defining a temperature control jacket chamber (water bath) 18 for holding the temperature of a fluid medium 24 constant inside the cylindrical vessel 12. The fluid medium 24 may comprise any dissolution medium suitable for use in drug dissolution testing. The particular medium is selected based upon the nature of the dosage form under study. The medium may comprise, for example, water, dilute hydrochloric acid, or phosphate buffers of various pH's.

Figure 2:
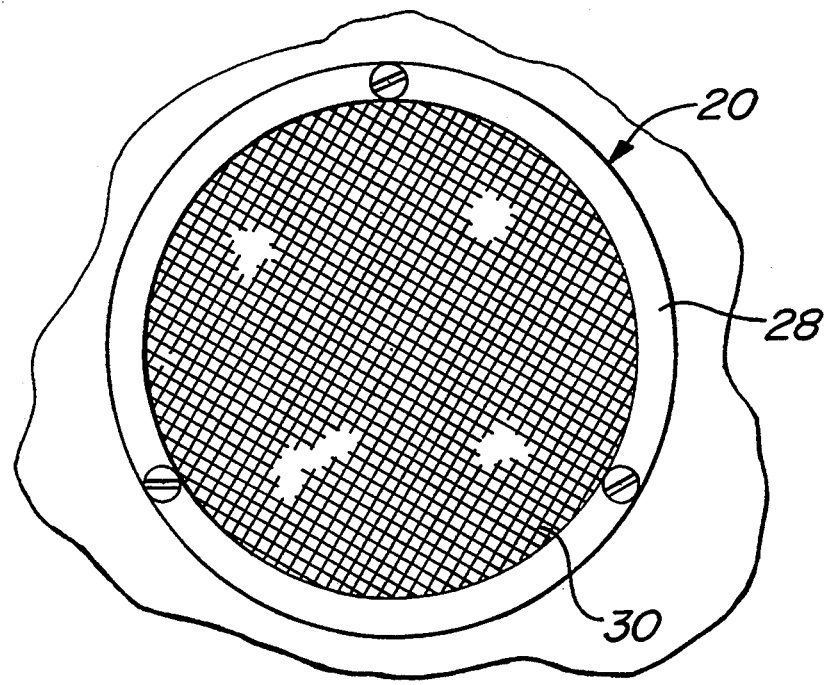
FIG. 2 is a top view of the disk taken along the line 2-2 in FIG. 1.

Located in the cylindrical vessel 12 is a disk 20 located approximately 40 millimeters from the lowermost portion 22 of the hemispherical bottom 14. Referring to FIGS. 1 and 2, the disk 20 has an annular ring assembly consisting of two tings 26 and 28 which circumferentially enclose a screen mesh 30. The mesh size is selected so as to permit the fluid medium 24 to flow through the disk and to limit upward movement of a dosage form 36 described below. Preferably the mesh size is a 40-size mesh formed by woven wires having a nominal wire diameter of 0.25 millimeter and openings of 0.37 mm. The diameter of the ring 26 is such that an outer edge 32 engages the sides of the vessel 12. The outer edge 32 has a convex curve portion 33 to conform with the complimentary concave sides of the vessel 12 when the disk 20 is located in the cylindrical vessel 12. The disk is spaced above the lowermost portion 22 of the bottom 14 consistently in the same horizontal plane therein defining a dosage form retaining space 34.

It is recognized that the location of the disk 20 relative to the lowermost portion 22 of the bottom 14 is dependent on the diameter of the rings 26 and 28, the diameter of the vessel 12, and the curvature of the bottom. However, the disk 20 must be spaced from the bottom 14 such that the dosage form retaining space 34 is large enough to allow free movement of the dosage form 36.

A dosage form 36 that is to be tested is placed in the cylindrical vessel prior to the insertion of the disk 20. The dosage form may comprise any solid or semisolid body comprising one or more drugs and one or more other materials adapted to form the body of the dosage form. The present invention is particularly well suited for determining the dissolution profile of gel-based dosage forms. Such forms are characterized by a drug-release matrix which is adapted to absorb fluid and swell, thereby increasing in volume. The swelling, however, causes gel-based dosage forms to float in the fluid medium.

In particular, such swellable dosage forms will comprise one or more drugs contained in a capsule or matrix formed by a hydrocolloid, such as one of the hydroxy celluloses. For example, diltiazem hydrochloride, which is a calcium channel blocker with coronary vasodilating activity used for the treatment of hypertension, is administered in the form of an extended release capsule comprising ethyl cellulose, hydroxypropyl methylcellulose and gelatin. Diazepam, used for the treatment of anxiety disorders, is administered in a capsule formed from hydroxypropyl methylcellulose. Other swellable formulations currently undergoing clinical studies contain 20–75% w/w hydrocolloids, such as hydroxyethyl cellulose, hydroxypropyl cellulose and hydroxypropyl methylcellulose.

The screen 30 of disk 20 limits the dosage form 36 to the dosage form retaining space 34 while allowing the fluid medium 24 to flow through the screen 30 and into retaining space 34.

According to known methods, a stirring element or paddle 38 depends into the cylindrical vessel 12 and has a vertical shaft 40 and blade 42 at the lower end of the shaft 40. The blade 42 passes through the bottom of the shaft 40 so that the bottom of the shaft 40 and the blade 42 are flush. The paddle is centered relative to the sides of the cylindrical vessel 12. However, distinct from previous method that do not employ a disk spaced from the vessel bottom defining the dosage retaining space 34, the bottom of the shaft 40 and blade 42 are spaced approximately 20 millimeters above the screen mesh 30 of the disk 20 (i.e. the paddle over disk). At the top end of the shaft-40 is a speed regulating device, not shown, for rotating the paddle 38 at a designated speed. The construction of the speed regulating device is conventional, and does not form a part of the present invention. The paddle 38 is held in position above the screen mesh 30 by either the placement of the speed regulating device or, alternatively, by a pair of collars 44 and 46. The collars sandwich a cover 48 positioning the paddle upon placement of the cover 48 on a flange 50 of the cylindrical vessel 12.

The construction and operation of the stirring element, including the speed regulation device, is conventional, and well-known in the art.

Dissolution Testing

The test apparatus is operated as follows to test the dissolution rate of the dosage form 36. The temperature control jacket chamber 18 is brought to the desired temperature, typically 37°±0.5° C. The dosage form 36 is placed within the dosage retaining space 34 of the cylindrical vessel 12. The disk 20 is inserted into the cylindrical vessel 12. The diameter of the outer ring 32 is selected such that disk 20 is positioned in the cylindrical vessel 12 at the proper distance relative to the lowermost portion 22 of the hemispherical bottom 14 as described above. The disk 20 defines the upper boundary of space 34 which is large enough for free movement of the dosage form 36. Disk 20 prevents the dosage form 36 from floating to the surface of the dissolution fluid.

The fluid medium 24, which has been brought to the proper temperature, is poured into the cylindrical vessel 12, and then the paddle 38 is lowered into the fluid medium 24 of the cylindrical vessel 12 such that the blade 42 is positioned above the disk 20. The cover 48 sits on the flange 50 of the cylindrical vessel 12 to limit evaporation of the fluid medium 24. The speed regulating device rotates the paddle 38 at the correct rate, for example 50 rotation per minute (rpm) therein creating a hydrodynamic effect to assist in the dissolution of the dosage form 36. The hydrodynamic effect created by the paddle 38 moves the dosage form 36 around in the space 34 resulting in the dosage form 36 not always engaging the screen mesh 30.

Figure 3:
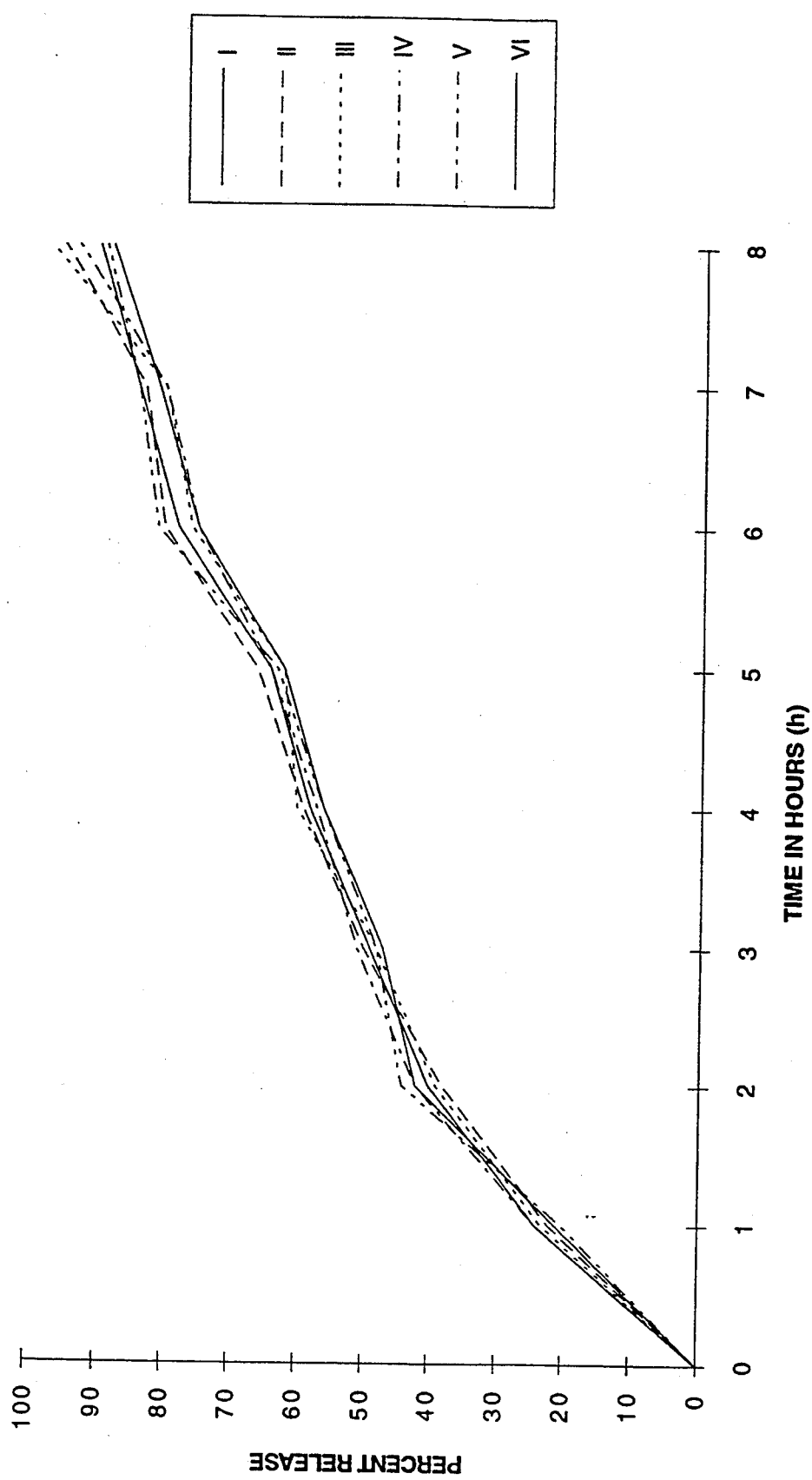
FIG. 3 is a graph showing the release of dexchlorpheniramine maleate from a swellable dosage form over time generated using the apparatus and method of the invention.
Figure 4:
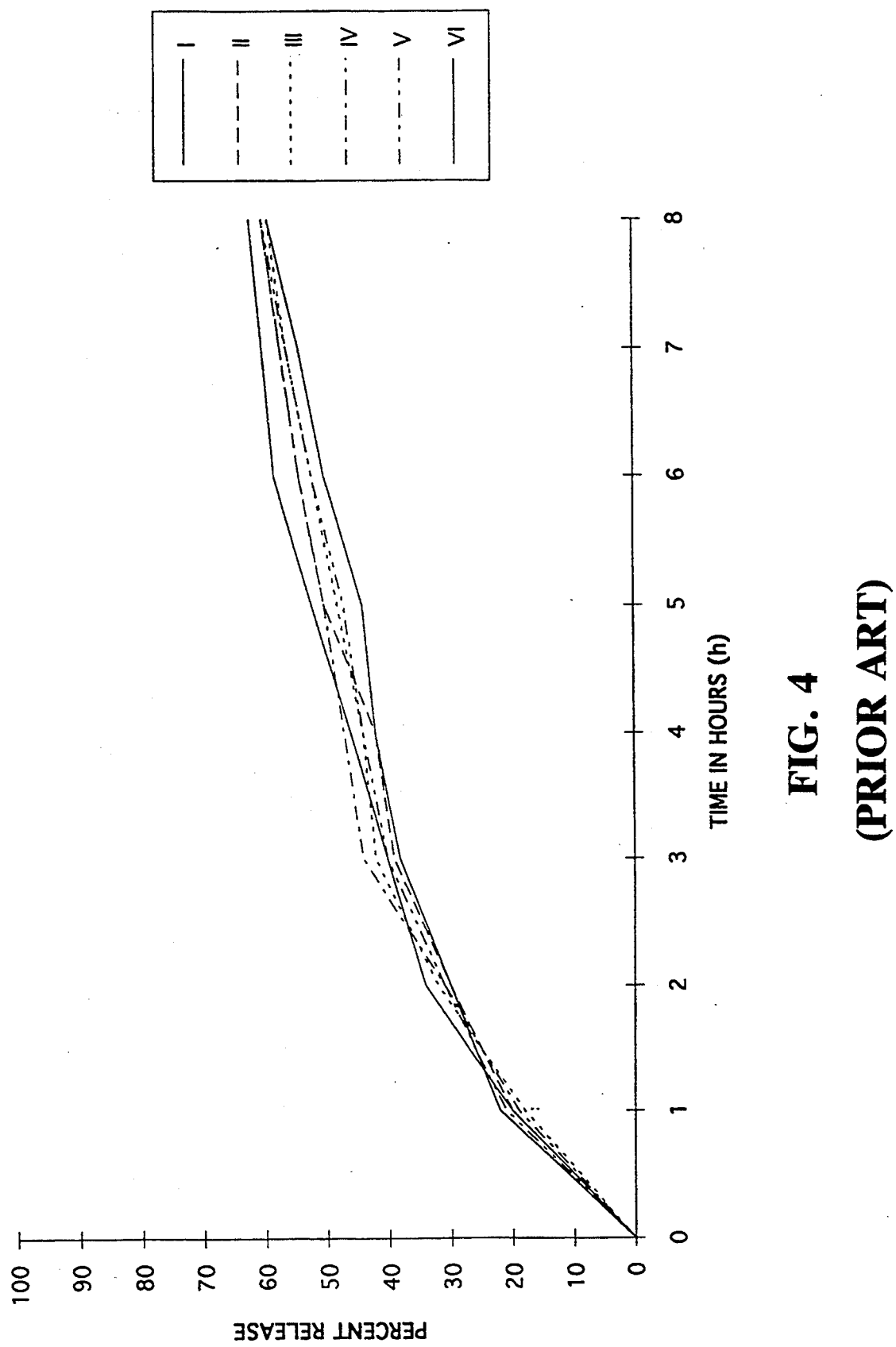
FIG. 4 is a graph similar to FIG. 3, generated using a prior art apparatus and method.

The dissolution profile of dosage form 36 is determined as follows. The fluid medium 24 is sampled at regulative intervals at a location spaced from the cylindrical vessel 12 and above the disk 20 by conventional methods. The drug concentration in each sample is determined. A dissolution profile similar to the graphs of FIGS. 3 or 4 is compiled from the data. The profile displays the behavior of the dosage form in releasing drug over time.

The present invention is more fully described in the following, non-limiting, illustrative example:

Tablets comprising 16 mg dexchlorpheniramine maleate (DM) in a matrix which is composed of gel forming material (hydroxypropylmethyl cellulose 90% w/w), a lubricant (magnesium stearate 2% w/w), and an inert ingredient (lactose 8%) were manufactured on an instrumented single punch machine (7 mm in diameter, 3 mm thickness) at about 100 MPa pressure. Twelve tablets of identical weight (having uniformity of content well within the *USP XXII* requirements) were tested for DM dissolution as follows, using vessel as described above.

Six tablets were tested using the paddle-over-mesh method procedure described above. The dosage form was placed in the vessel 12 and a disk having a 40-mesh described above was inserted. Distilled water at 37° C. was added as the dissolution medium. The paddle was positioned so that it was 20 millimeter above the mesh and the mesh was located 40 millimeters above the lowermost point 22 of the hemispherical bottom 14. The paddle was rotated at a speed of 50 rpm. DM concentration in the fluid medium was sampled at hourly intervals for 8 hours. Table 1 and FIG. 3 represent the release profiles for 6 tablets (I–VI).

TABLE 1

| DEXCHLORPHENIRAMINE MALEATE RELEASE FROM SWELLABLE DOSAGE FORM USING PADDLE OVER MESH DISSOLUTION METHOD | | | | | | |
|---|---|---|---|---|---|---|
| TIME | % RELEASE | | | | | |
| (h) | I | II | III | IV | V | VI |
| 0 | 0 | 0 | 0 | 0 | 0 | 0 |
| 1 | 24 | 22 | 23 | 24 | 20 | 21 |
| 2 | 40 | 38 | 39 | 42 | 44 | 42 |
| 3 | 49 | 50 | 48 | 51 | 48 | 47 |
| 4 | 58 | 59 | 60 | 57 | 56 | 56 |
| 5 | 64 | 66 | 62 | 64 | 63 | 62 |
| 6 | 78 | 80 | 76 | 75 | 81 | 75 |
| 7 | 84 | 83 | 80 | 80 | 84 | 81 |
| 8 | 90 | 95 | 97 | 93 | 89 | 88 |

The remaining six tablets were tested according to the procedure described in the *USP XXII* for dissolution of floatable dosage forms. The same cylindrical vessel assembly as described above was employed, except that in place of the disk 20, a wire helix of a few turns was attached to the dosage form to prevent floating. The paddle was placed 25±2 mm from the lowermost point of the hemispherical bottom rotating at 50 rpm. The fluid medium was 37° C. distilled water. Table 2 and FIG. 4 represent release profiles for these 6 tablets.

TABLE 2

DEXCHLORPHENIRAMINE MALEATE RELEASE FROM SWELLABLE MATRIX USING NON-REACTIVE WIRE HELIX TO PREVENT FLOATING

| TIME | % RELEASE | | | | | |
|---|---|---|---|---|---|---|
| (h) | I | II | III | IV | V | VI |
| 0 | 0 | 0 | 0 | 0 | 0 | 0 |
| 1 | 20 | 20 | 18 | 19 | 21 | 22 |
| 2 | 34 | 30 | 32 | 31 | 31 | 30 |
| 3 | 40 | 39 | 42 | 44 | 40 | 38 |
| 4 | 46 | 42 | 44 | 47 | 44 | 42 |
| 5 | 52 | 50 | 48 | 50 | 47 | 44 |
| 6 | 58 | 54 | 52 | 54 | 52 | 50 |
| 7 | 60 | 57 | 56 | 57 | 56 | 54 |
| 8 | 62 | 60 | 59 | 60 | 60 | 59 |

The six paddle-over-mesh release profiles of FIG. 3 are very similar, with about 90% drug release over an eight hour period. The six release profiles of the FIG. 4 prior art method are also similar. However, greater variation between the individual profiles is evident. Moreover, the total amount of drug released after 8 hours did not exceed 62% according to the prior art method. These differences are extremely significant. The variable and incomplete drug release evident in FIG. 4 is due to the fact that the main dissolution control mechanism, namely the swelling of the dosage form and diffusion of drug therefrom, is hindered by the wire-helix and thus does not reflect the true drug release pattern. The prior art helix coil dissolution method does not appear to correctly simulate the drug release pattern which would occur in vivo.

This study highlights the ease with which one can determine the actual release behavior of floating systems by adapting and using the invention presented here.

The present invention may be embodied in other specific forms without departing from the spirit or essential attributes thereof, and, accordingly, reference should be made to the appended claims, rather than to the foregoing specification, as indicating the scope of the invention.

I claim:

1. An apparatus for testing the dissolution of a dosage form, comprising:
   an inert cylinder vessel adapted to hold a fluid medium having a bottom;
   a stirring mechanism depending into the vessel for rotating the fluid medium; and
   a disk positioned in the vessel adapted to engage the vessel wall at a location spaced from the vessel bottom, the disk having a plurality of holes for passage of the fluid medium therethrough; and
   the disk lower surface and the vessel bottom defining a dosage form retaining space for retaining and allowing movement of the dosage form in the volume between the vessel bottom and the disk.

2. An apparatus according to claim 1 wherein the disk has a screen mesh having the plurality of holes.

3. An apparatus according to claim 2 wherein the cylindrical vessel is transparent and the bottom is hemispherical with concave surface facing upward.

4. An apparatus according to claim 3 wherein the stirring mechanism is a paddle having a blade at a lower end of a shaft.

5. An apparatus according to claim 4 wherein the screen mesh of the disk is spaced from the bottom of the vessel by a distance of from about 35 millimeters to about 45 millimeter and spaced from the paddle by a distance of from about 17 millimeter to about 23 millimeters.

6. An apparatus for testing dissolution of a swellable, floatable dosage form comprising:
   an inert, transparent cylindrical vessel adopted to hold a fluid medium having a hemispherical concave bottom;
   a stirring mechanism having a vertical shaft adapted to depend into the fluid medium and a blade at a lower end of the shaft for rotating the fluid medium; and
   a disk positioned in the vessel spaced from the vessel bottom, the disk comprising a pair of annular rings adapted to engage the vessel and a screen mesh circumferentially sandwiched by the rings to allow passage of the fluid medium through the disk screen mesh;
   a dosage form retaining space defined by the volume intermediate to the disk and the vessel bottom for containing the dosage form.

7. An apparatus according to claim 6 wherein the screen mesh of the disk is spaced from the bottom of the vessel by a distance of from about 35 millimeters to about 45 millimeter and spaced from the paddle by a distance of from about 17 millimeter to about 23 millimeters.

8. An apparatus for limiting floatation of a dosage form in a drug dissolution testing vessel comprising an annular ring assembly circumferentially enclosing and surrounding a screen mesh, the ring assembly having an outwardly circumferentially edge for contacting the vessel wall a selected distance from the vessel bottom to form a dosage form retaining space defined by the volume intermediate to the disk and the vessel bottom.

9. An apparatus according to claim 8 wherein the annular ring assembly comprises first and second concentric mating annular rings sandwiching the screen mesh between the peripheral edges of said first and second annular rings.

10. A method for testing the dissolution of a drug from a dosage form comprising:
    providing an inert cylindrical vessel having a hemispherical concave bottom containing a fluid medium;
    placing the dosage form in the vessel;
    inserting a disk into the vessel which engages the vessel wall at a location above the dosage form, thereby forming a dosage form retaining space for retaining the dosage form in the fluid volume under the disk, the disk having a plurality of holes for passage of the fluid medium therethrough;
    inserting a stirring mechanism having a vertical shaft and a blade at a lower end of the shaft into the vessel;
    rotating the stirring mechanism to circulate the fluid medium in the vessel;
    sampling the drug concentration in the fluid medium at selected time intervals.

11. A method according to claim 10 wherein the disk comprises an annular ring circumferentially enclosing a screen mesh.

12. A method according to claim 10 wherein the dosage form is swellable, floatable dosage form and the disk limits upward movement of the swellable, floatable dosage form in the fluid medium.

13. In combination an apparatus and dosage form for testing of the dosage form, the combination comprising:

an inert cylindrical vessel adapted to hold a fluid medium having a bottom, a stirring mechanism depending into the vessel for rotating the fluid medium, and a disk positioned in the vessel adapted to engage the vessel wall at a location spaced from the vessel bottom, the disk having a plurality of holes for passage of the fluid medium therethrough;

a swellable, floatable dosage form adapted for three dimensional swelling and a drug release over a specific period of time; and a dosage form retaining space defined by the volume intermediate to the disk and the vessel bottom for retaining and allowing floating and swelling of the dosage form between the vessel bottom and the disk.

* * * * *